United States Patent
Conway

(10) Patent No.: US 6,536,423 B2
(45) Date of Patent: Mar. 25, 2003

(54) PATIENT ACTIVATED MOUTH MOISTURIZER

(75) Inventor: Patrick J Conway, 7034 Harbour Village Ct., #202, Annapolis, MD (US) 21403

(73) Assignee: Patrick J Conway, Annapolis, MD (US)

( * ) Notice: Subject to any disclaimer, the term of this patent is extended or adjusted under 35 U.S.C. 154(b) by 0 days.

(21) Appl. No.: 09/863,345

(22) Filed: May 24, 2001

(65) Prior Publication Data

US 2002/0017292 A1 Feb. 14, 2002

Related U.S. Application Data

(60) Provisional application No. 60/224,509, filed on Aug. 14, 2000.

(51) Int. Cl.$^7$ ................................................ A61B 19/00
(52) U.S. Cl. .......................... 128/200.14; 128/200.21; 128/200.23; 128/204.15; 289/338
(58) Field of Search ..................... 128/200.14, 200.15, 128/200.21, 200.23, 204.15, 200.16; 239/338

(56) References Cited

U.S. PATENT DOCUMENTS

| | | | | |
|---|---|---|---|---|
| 3,379,194 A | * | 4/1968 | Ziermann ................ 128/145.6 |
| 4,551,139 A | * | 11/1985 | Plaas et al. .................. 604/290 |
| 4,582,054 A | * | 4/1986 | Ferrer .................... 128/200.23 |
| 4,679,551 A | * | 7/1987 | Anthony ................. 128/200.16 |
| 4,955,371 A | * | 9/1990 | Zamba et al. ........... 128/200.18 |
| 5,062,795 A | * | 11/1991 | Woog .......................... 433/80 |
| 5,483,953 A | * | 1/1996 | Cooper .................. 128/200.14 |
| 5,701,885 A | * | 12/1997 | Hale ...................... 128/201.11 |
| 6,021,776 A | * | 2/2000 | Allred et al. ........... 128/200.14 |
| 6,244,266 B1 | * | 6/2001 | Margiotta, Jr. ......... 128/200.24 |

* cited by examiner

Primary Examiner—Gregory L. Huson
Assistant Examiner—Azy Kokabi
(74) Attorney, Agent, or Firm—Fisher, Christen & Sabol

(57) ABSTRACT

A patient recovering from major surgery often suffers from cracked lips and parched palate. The patient usually frequently contacts the nursing staff and requests that they provide the patient with cool water and/or cracked ice. The amount of water and/or cracked ice which the patient can have has to be very limited in order to prevent debilitating vomiting by the patient. The patient's discomfort and suffering is greatly reduced by the mouth moisturizer which via an atomizer supplies a controlled amount of water mist to the lips and palate of the patient. Also, the nurses have more time to devote to their other duties.

33 Claims, 9 Drawing Sheets

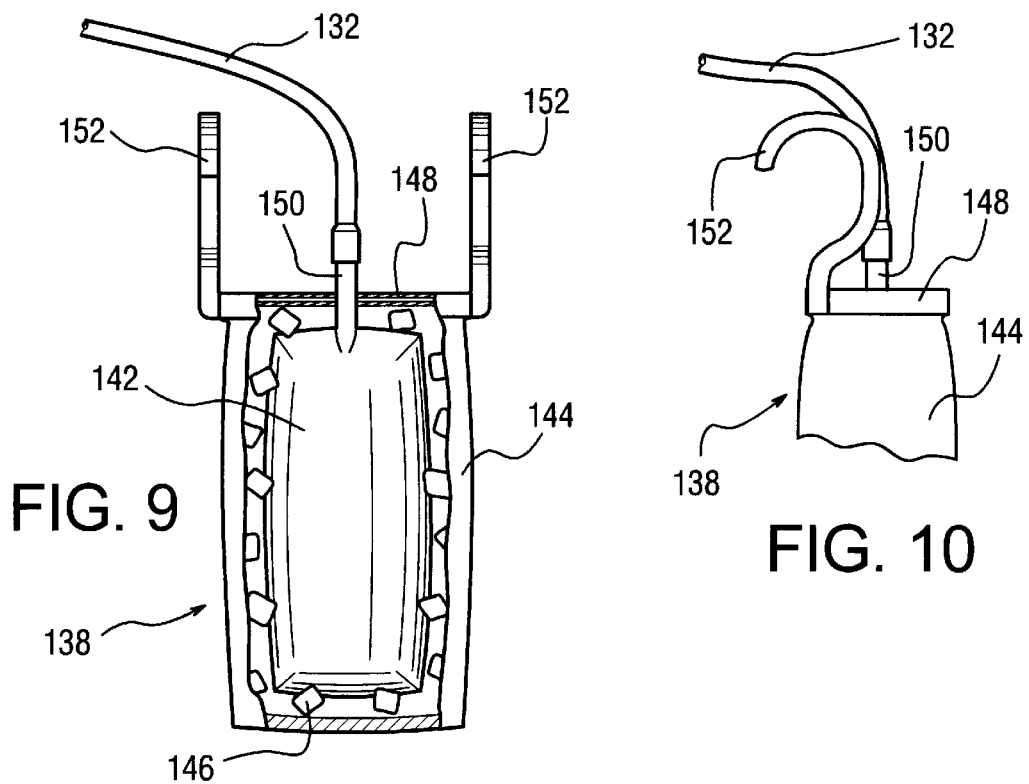
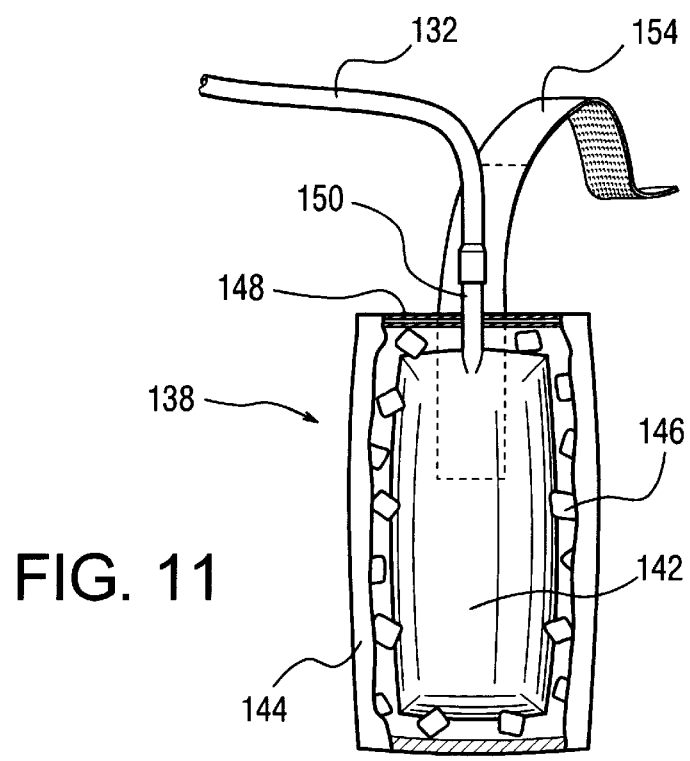

PATIENT ACTIVATED MOUTH MOISTURIZER

This application has benefit of U.S. Provisional Application Ser. No. 60/224,509, filed on Aug. 14, 2000.

BACKGROUND OF THE INVENTION

1. Field of the Invention

The invention relates to patient activated mouth moisturizer systems and methods of using such systems.

2. Background Art

The first several days of the post-operative period after surgery, usually so-called major surgery, often involves difficulties, discomfort and problems for a patient. From the patient's point of view, one of the most difficult experiences connected to major surgery is the occurrence of cracked lips and parched palate that goes on for several days after surgery. Normally the patient is allowed only very limited amounts of water or cracked ice in order to prevent vomiting or so-called "dry heaving" by the patient. Vomiting can cause serious stress on the body and other problems to the patient. The patient very often suffers substantially from being given only the small amounts of water or cracked ice.

Because of the patient's discomfort and suffering, the patient, seeking relief, tends to make many calls day and night to the nursing staff. The nurses then spend much time repeatedly providing the patient small amounts of cool water and/or chipped ice. The nurses are thereby kept from performing other important duties.

Infirm and sick residents and patients in nursing homes and facilities which provide long term care often experience discomfort and suffering from chronic and short term conditions which result in cracked lips and parched palate. The providing of small amounts of cool water and/or cracked ice to the residents or patients who need it, whether short term or over extended periods, is perhaps more of a problem than it is with hospitals since the ratio of patients to nurses is usually much higher in nursing homes. Experience shows that the ratio usually becomes even higher on weekends and most holidays.

BROAD DESCRIPTION OF THE INVENTION

An objective of the invention is to provide a system which addresses/relieves the patient's discomfort and suffering and which relieves the nursing staff of the time consuming task of providing cool water and/or crushed ice for the patient.

Other objectives and advantages of the invention are set out herein or are obvious to one skilled in the art herefrom.

The objectives and advantages of the invention are achieved by the systems, devices and process of the invention.

Broadly speaking, the system of the invention provides controlled aqueous liquid or moisture in the form of a mist to the mouth and/or lips of the patient. Preferably a cool water mist is provided. The invention system preferably is capable of providing a predetermined amount of water mist in a predetermined amount of time to the patient whereby the patient is unable to provide himself with an excess of water and thereby avoiding vomiting problems.

The mouth moisturizer system of the invention includes means for atomizing an aqueous liquid with a gas to form a mist which is supplied in a controlled manner to the patient's lips and/or mouth. The mist-forming end of the atomizer means is adapted to fit in the patient's mouth. There is also means for providing the aqueous liquid and the gas to the atomizer means.

A patient recovering from major surgery often suffers from cracked lips and parched palate. The patient usually frequently contacts the nurses and requests that they provide the patient with cool water and/or cracked ice. The amount of water and/or cracked ice which the patient can have has to be very limited in order to prevent debilitating vomiting by the patient. The patient's discomfort and suffering is greatly reduced by the mouth moisturizer which via an atomizer is capable of supplying a controlled amount of water mist to the lips and/or palate of the patient over a controlled amount of time. Also, the nurses have more time to devote to their other duties.

The system of the invention is also useful for use by short term and long term residents/patients in nursing homes and other care facilities.

The invention involves a mouth moisturizer system comprising: (a) means for atomizing an aqueous liquid with a gas to form a mist which is supplied in a controlled manner to lips and/or the mouth of a person, a portion of said atomizing means being adapted to fit in the mouth of the person; and (b) means for providing the aqueous liquid and the gas to the atomizer means.

The aqueous liquid is usually water and is preferably distilled or sterilized water. The gas is usually air. The gas should be safe and nontoxic.

Preferably means (b) includes a gas compressor and a tube for transportation of pressurized gas from the gas compressor to the atomizer means. Preferably means (b) further includes a tube for transportation of pressurized aqueous liquid from a source of pressurized aqueous liquid to the atomizer means. Preferably the means (b) additionally includes a pump for pressurizing the aqueous liquid, and a tube for transportation of the pressurized aqueous liquid from the pump to the atomizer means.

Preferably means (b) includes means to control the frequency of and duration of operation of the gas compressor and the aqueous liquid pump. In this manner the amount of aqueous liquid mist which can be delivered to the patient over a time period can be controlled. An adjustable timer, that is inaccessible to the patient, is advantageous.

Preferably the mouth moisturizer system also includes a container of aqueous liquid in a unit which is adapted to be mounted on the frame of the patient's bed, and a tube for transporting the aqueous liquid from the container to the aqueous liquid pump.

Preferably the atomizer means (a) comprises an elongated atomizer unit which has a fin which is situated perpendicular to its longitudinal axis and which totally or substantially extends around its circumference. Moist providing end of the elongated atomizer unit is capable of being positioned in the patient's mouth.

Also preferably the atomizer means (a) comprises a base which has a curved groove which fits over the lower gum or at least some of the lower teeth of the patient, and an elongated atomizer unit is mounted on said base so that moist providing portion of said elongated aerator unit is capable of being positioned in the patient's mouth.

Further preferably the atomizer means (a) comprises an atomizer unit having an elongated central portion and two diametrically opposed arm portions. The atomizer unit is capable of providing mist out of at least one aperture in each of the two arms of and/or at least one aperture in the end of the elongated central portion which extends into the patient's mouth. In a variation there is an extension on the end of each arm, and elastic band means attached to the unattached end of the arm extensions capable of holding the atomizer unit in the mouth of the patient.

The invention also includes a process of moisturizing lips and/or mouth of a patient comprising: (i) forming a mist by aerating an aqueous liquid with a gas, and (ii) supplying the mist to the lips and/or mouth of the patient.

Where the patient is recovering from major surgery, preferably the aqueous liquid is water and preferably the gas is air. Preferably the water is cooled, sterilized water. Advantageously the mist is directed at the lips and/or into the mouth of the patient. The supplying of the mist to the patient is preferably done in a controlled manner such that the patient obtains only a predetermined amount of water in a predetermined amount of time.

BRIEF DESCRIPTION OF THE DRAWINGS

In the drawings:

FIG. 9 is a partially cutaway, back elevational view of one version of the water supply system;

FIG. 10 is a partial left side elevational view of the water supply system of FIG. 9;

FIG. 11 is a partially cutaway, back elevational view of another version of the water supply system;

DETAILED DESCRIPTION OF THE DRAWINGS

The aqueous liquid is preferably sterilized or distilled water. For more relief for the patient, the water should be cooled. The aqueous liquid can be composed of water and any other suitable additives, such as, flavorants, e.g., wintergreen and peppermint, and therapeutic additives.

The gas is preferably air, but can also be air reinforced with any other suitable gaseous component(s), such as, gaseous therapeutic additives.

The preferred version of mouth moisturizer system 100 of the invention, except for mouthpiece 102, is shown. The preferred version of mouthpiece 102 is shown in FIGS. 12 to 16.

Figure 2:
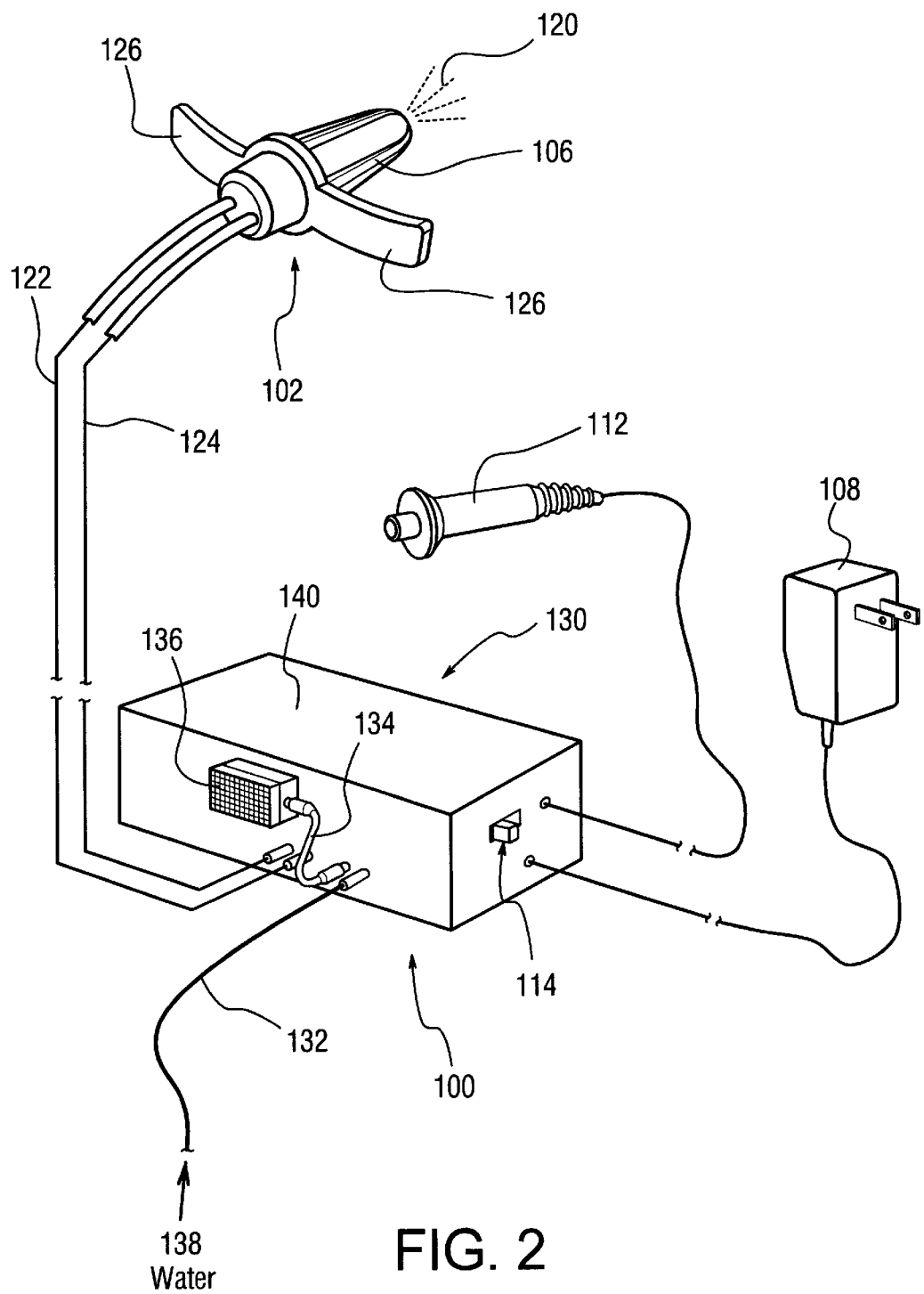
FIG. 2 is a top perspective view of one version of the mouth moisturizer system of the invention, including the mouthpiece of FIG. 1.
Figure 3:
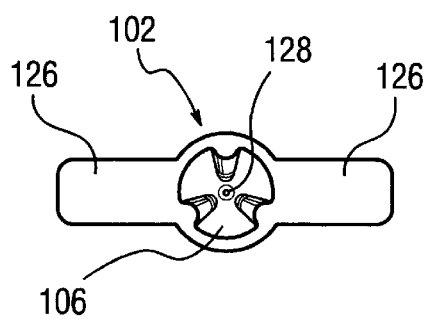
FIG. 3 is a front elevational view of the mouthpiece of FIG. 1.
Figure 4:
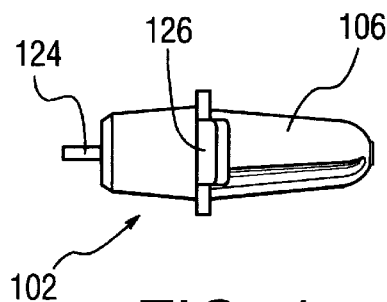
FIG. 4 is a left side elevational view of the mouthpiece of FIG. 1.
Figure 5:
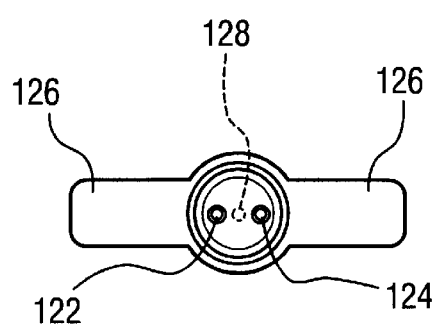
FIG. 5 is a back elevational view of the mouthpiece of FIG. 1.
Figure 8:
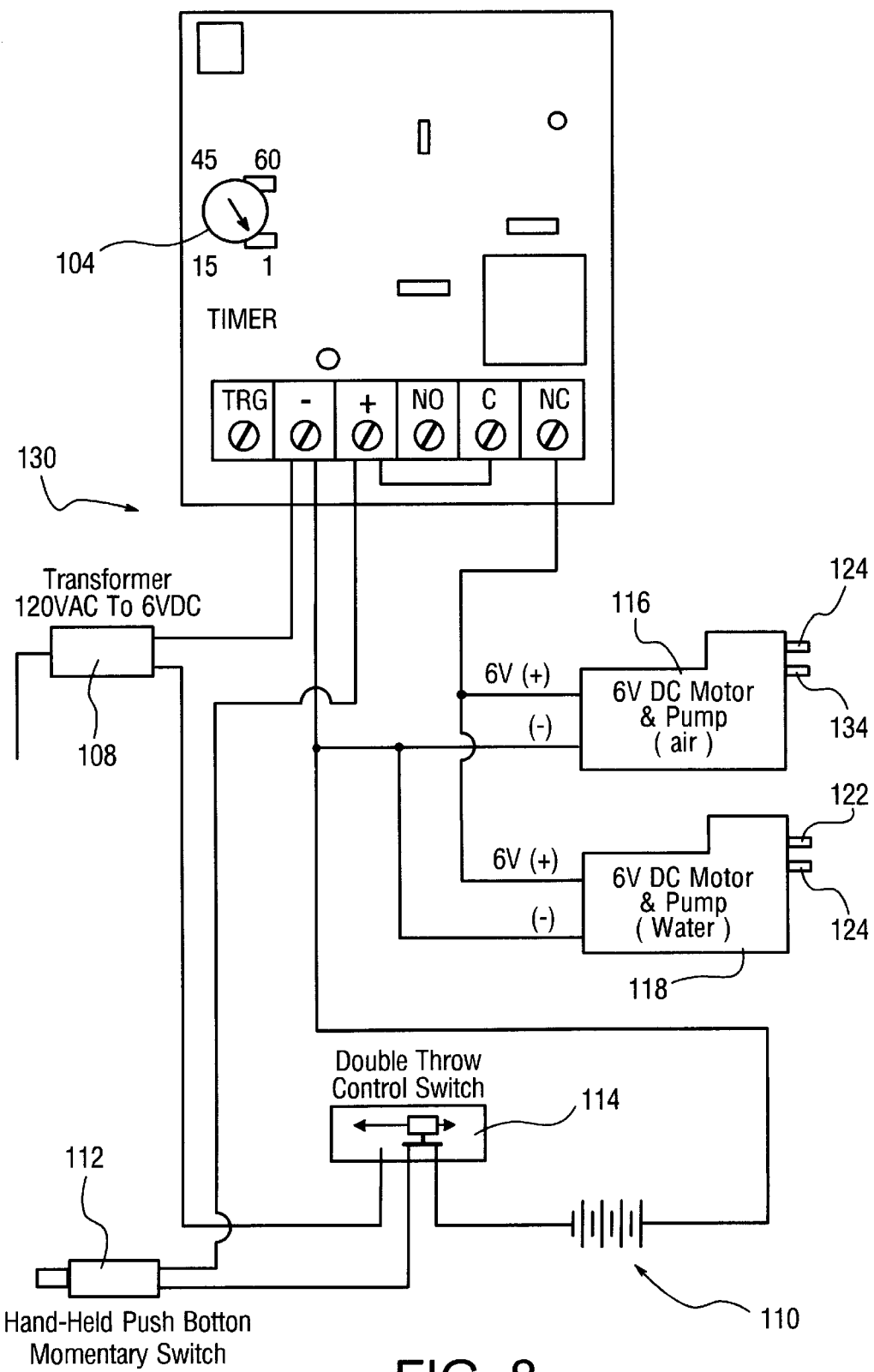
FIG. 8 is a diagram of the components and mini-pump module of the invention.
Figure 12:
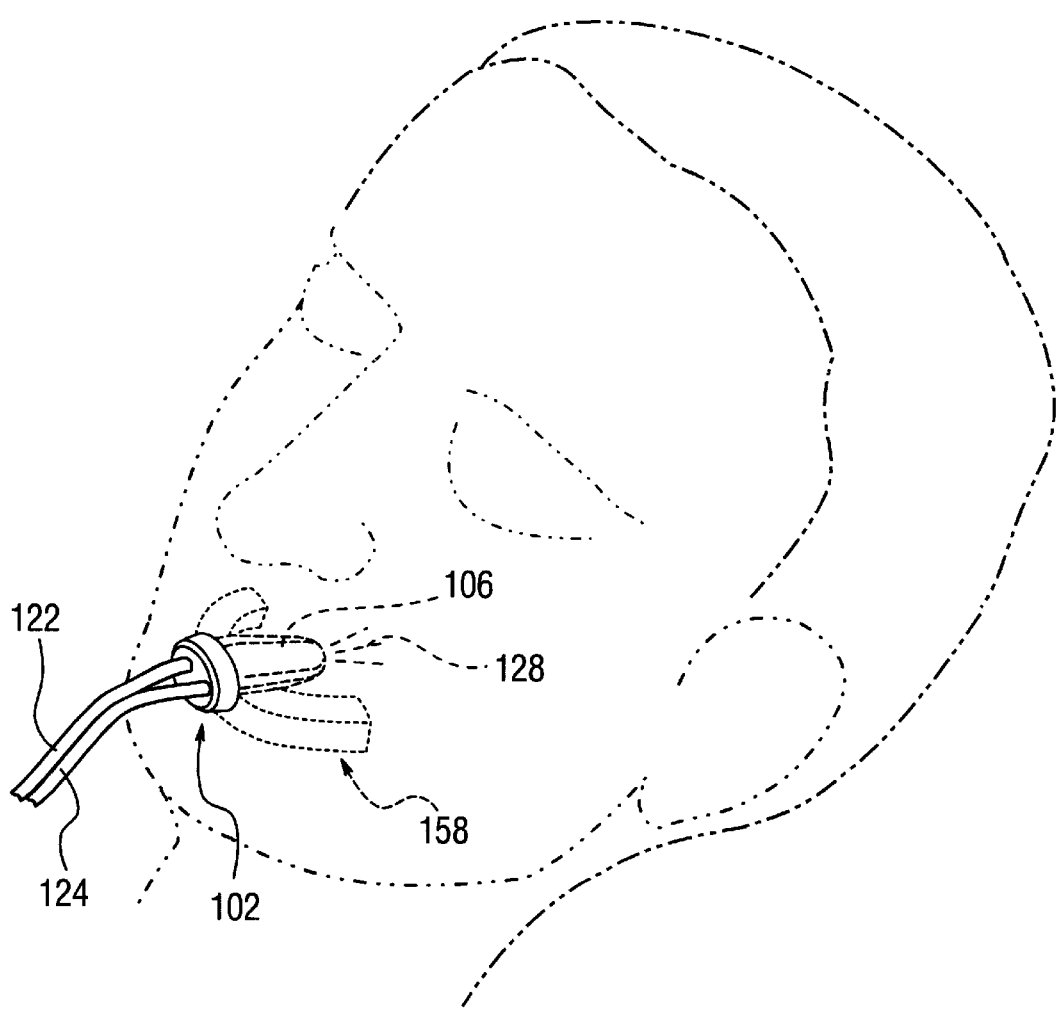
FIG. 12 is a top perspective view of a further mouthpiece of the invention.
Figure 13:
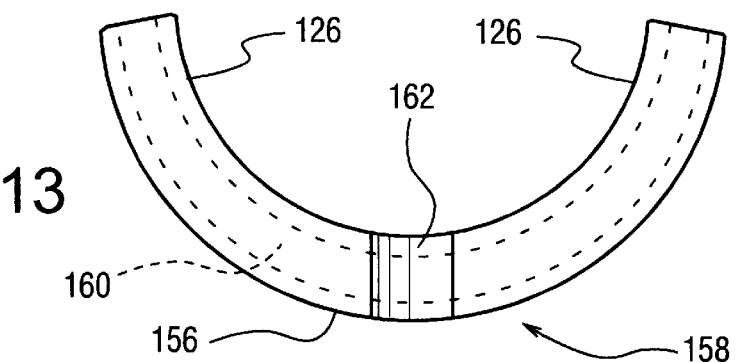
FIG. 13 is a top elevational view of the mouthpiece of FIG. 12.
Figure 14:
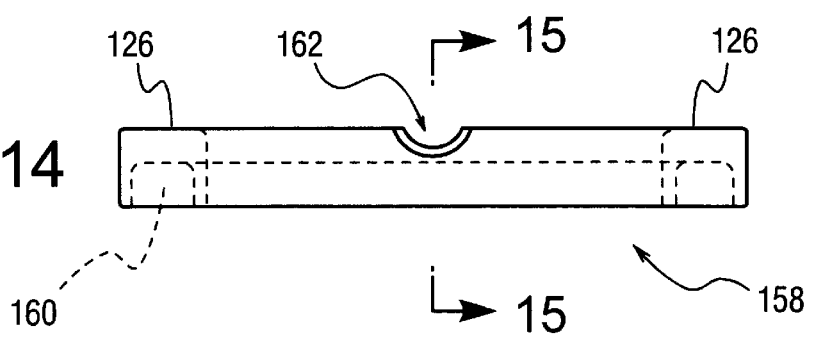
FIG. 14 is a front elevational view of the mouthpiece of FIG. 12.
Figure 15:
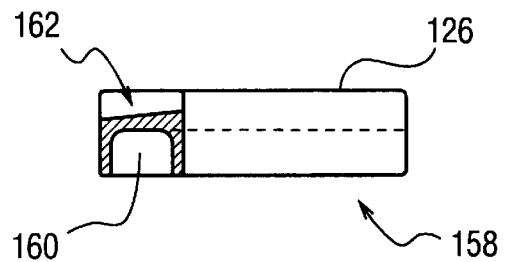
FIG. 15 is a sectional view along line 15—15 in FIG. 14.
Figure 16:
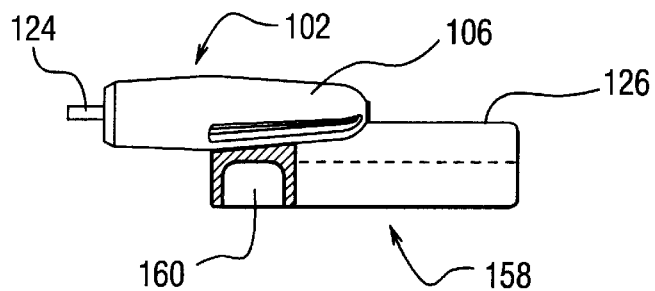
FIG. 16 is a sectional view along line 15—15 in FIG. 14 with the atomizer in place.

In FIG. 2, mini-pump(s) module 130 has two pumps 116 and 118 (not shown in FIG. 2, but see FIG. 8). Air is supplied to air pump 116 via air supply line 134 which has air filter 136 at its intake. Water is supplied to water pump 118 via water supply line from water source 138 (see FIGS. 9 to 11). Hand-held push button controller (momentary switch) 112 allows the patient to activate the mouth moisturizer system 100. Power is supplied for mouth moisturizer system 100 by internal batteries 110 (not shown) or by wall plug transformer 108. Use of power source 108 or 110 is made via double throw control switch 114.

Figure 1:
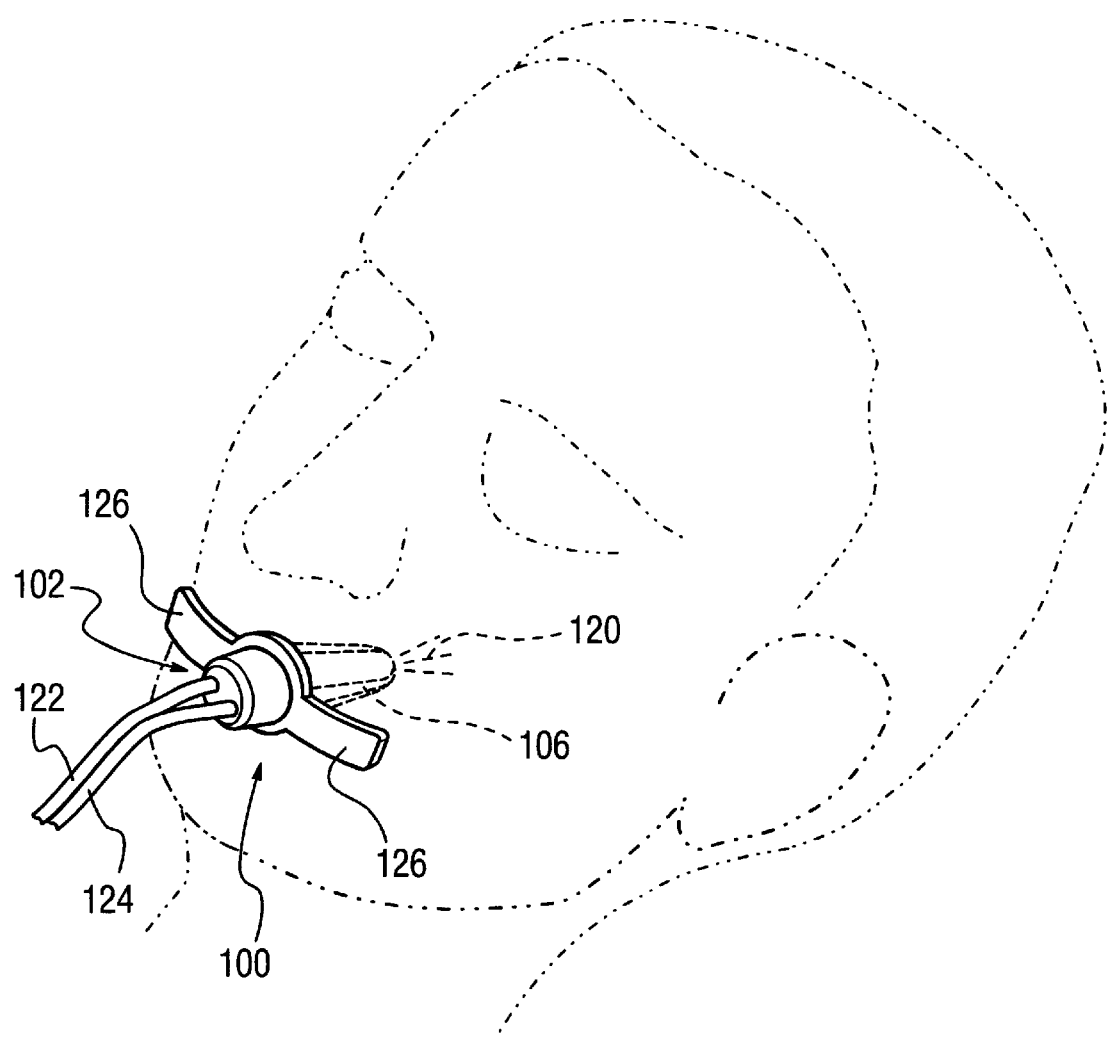
FIG. 1 is a top perspective view of one version of the mouthpiece, including the atomizer, of the invention.
Figure 6:
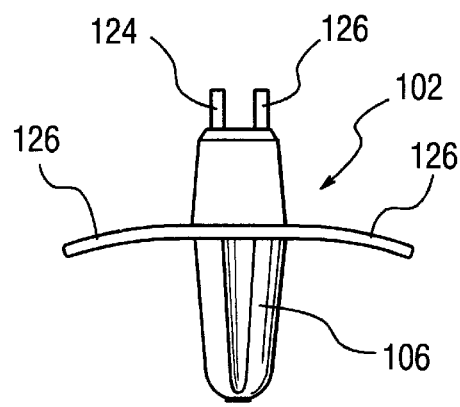
FIG. 6 is a top elevational view of the mouthpiece of FIG. 1.
Figure 7:
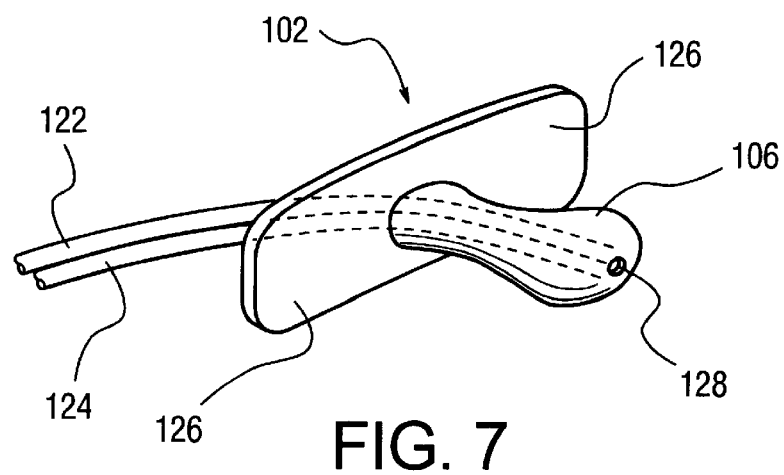
FIG. 7 is a top perspective view of another mouthpiece of the invention.

Referring to FIGS. 1 and 6, mouthpiece 102 has centrally located atomizer 106, which has a conventional atomizing chamber (not shown) wherein a water mist is formed. Air pump/compressor 116 supplies slightly pressurized air via tube/line 124 to the downstream side of atomizer 106. Water pump 118 supplies slightly pressurized water via tube/line 122 to the downstream side of atomizer 106. As shown in FIG. 1, the front or upstream end of atomizer 106 easily fits into the patient's mouth with curved fins or side arm plates 126 keeping atomizer 106 from entering too far into the patient's mouth. In this manner, swallowing of mouthpiece 106 by the patient is prevented. The water mist exits via aperture 128 of atomizer 106 into the patient's mouth. Mouthpiece 102 preferably is a disposable unit made of plastic.

Versions of water source 138 are shown in FIGS. 9 to 11. Bag/package 142 of sterilized water is positioned in insulated container 144 with ice pieces 146 surrounding bag 142. In this way, the water can be cooled for up to 24 hours. Water bag 142 is advantageously of sufficient size to hold 1000 ml of commercial sterilized water. Insulated top 148 is removable, for example, screwed onto the top of container 144. Probe tube segment 150 is positioned through insulated container top 148. The outer end of probe tube 150 is affixed to water supply line 132. The inner end of probe tube 150 is inwardly slanted with a sharp blade end and penetrates into water bag 142.

Water bag 142 can be hung as is done with an intravenous bag.

Preferably water container 144 can be hung from the bedside railing or other part of the bed frame. Advantageously, as shown in FIGS. 9 and 10, two hooks 152 can be mounted diametrically from each other on one side of container top 148 and are used for hanging water container 144 on the bedside railing, for example. Or, advantageously, strap 154 composed on one side of "VELCRO" or other hook-loop attachment material is affixed to the side of container 144 and is used for hanging water container 144 on the bed frame railing, for example.

Timer 104 allows control of the amount of water mist provided over or within a certain time period. The frequency and length of the mist formation by atomizer 106 can be preset. In this manner, timer 104 is a frequency controller. The frequency period can be preset at the factory/supplier and can be adjusted by the hospital, but not the patient. Timer 104 typically will have two time settings, for example, one setting allowing operation of atomizer 106 for a certain time period, typically for one second, and another setting to allow operation of atomizer 106 again until after a certain amount of time has passed, typically two minutes.

FIG. 8 shows how the components and controls for the mini-pump module 130 are connected. The sequence of operation is as follows for this connection:

1. Once unit 100 is powered by wall plug transformer 108 or batteries 110, hand held pushbutton 112 is connected and activated, 6v dc is sent to battery/wall transformer selector switch 114 and onto timing device 104 which is adjustable from 1 to 60 seconds.

2. If timer 104 is set for one second, the user can hold the pushbutton 112 and pumps 116 and 118 will dispense water and air for one second and timer 104 will open the circuit. The user can activate pumps 116 and 118 for the next delivery of water right after the last cycle stops or only after a predetermined period of time.

3. If the user continuously holds pushbutton 112 intentionally or by accident, pumps 116 and 118 will not operate after the last cycle until pushbutton 112 is released and reactivated (and any preset time activation interval has passed).

Mini-pump module 130 system of FIG. 8 can be used with any of the versions of mouthpieces 102/atomizers 106 shown in the drawings.

Batteries 110 are advantageously 4 AA batteries, or 2 9v batteries. Longer usage life is obtained with the latter.

Hand-held controller 112 satisfactorily is the "Hand-Held Pushbutton with Cord", (Catalog No. PB-95), of All Electronics Corp., (1-888-826-5432); it has a normally-open, momentary switch.

Any suitable transformer can be used for transformer . . . when an outside power source is used. Transformer 108 satisfactorily is the transformer, Globtek Part No. WR91B1000LCP-Y, of Globtek, Inc., Northvale, N.J.; its output voltage is 6v dc.

Any suitable air pump/compressor can be used. Air pump 116 satisfactorily is Model 30, AAA Series Micro Air Pump, Sensidyne, Inc. outside of a patient's lips. This shape allows the patient to more easily hold atomizer 106 between his teeth without it slipping out. Fins 126 prevent mouthpiece 102 from being swallowed because they protrude past/beyond the mouth opening.

FIGS. 12 to 16 show the preferred version of mouthpiece 102. Central portion 156 and side fins 126 of mouthpiece 102 forms the generally C-shape securement rim 158 which correlates to the shape of the lower gum. Bottom groove 160 on the bottom of securement rim 158 fits over the teeth in the lower gum of the patient. Top groove 162 is perpendicular to the central axis of securement rim 158. Atomizer 106 is affixed (e.g., glued) in top groove 162 with its mist-producing end extending inward from the patient's teeth.

Figure 17:
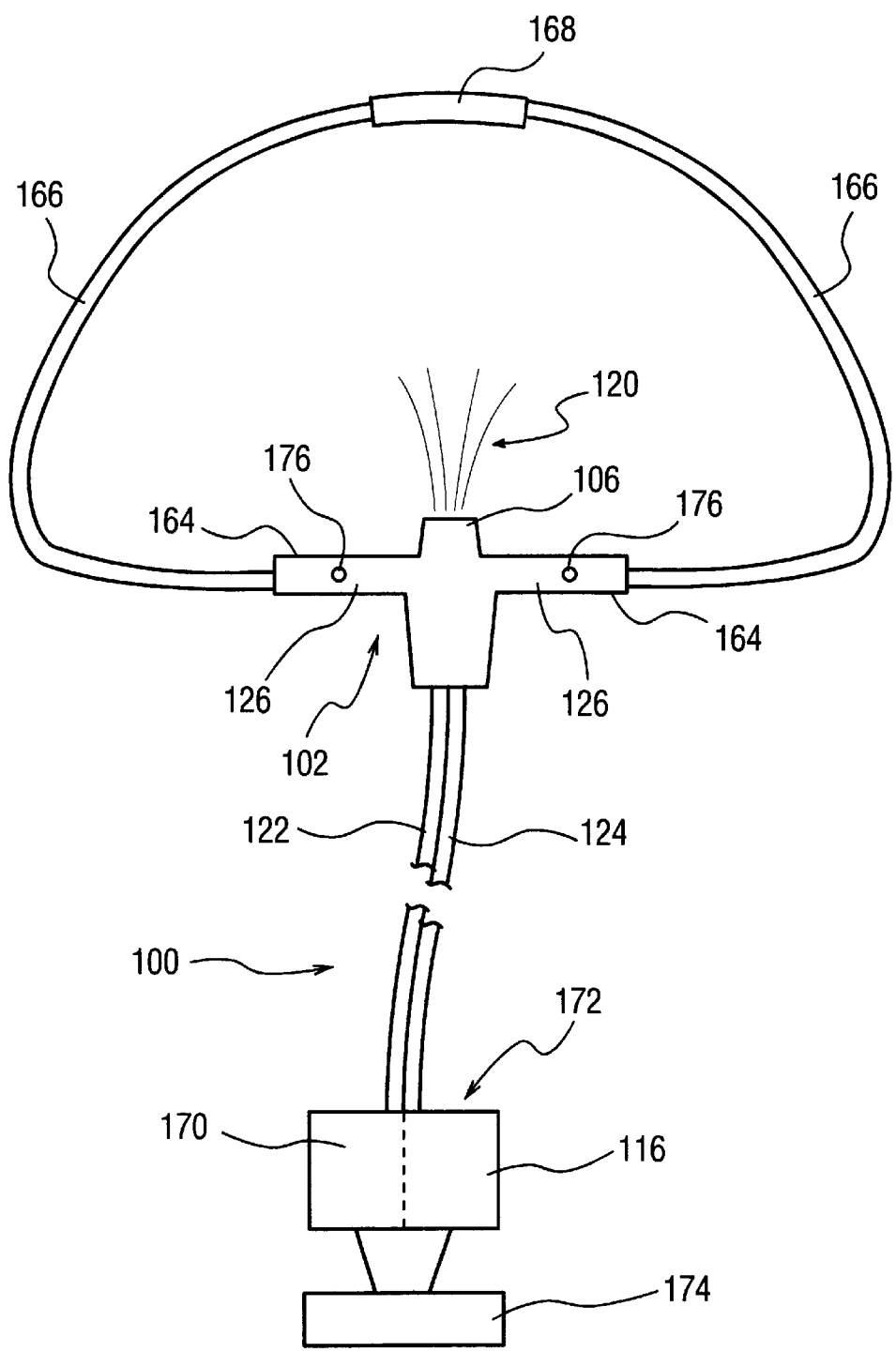
FIG. 17 is a top elevational view of another version of the mouth moisturizer system of the invention.
Figure 18:
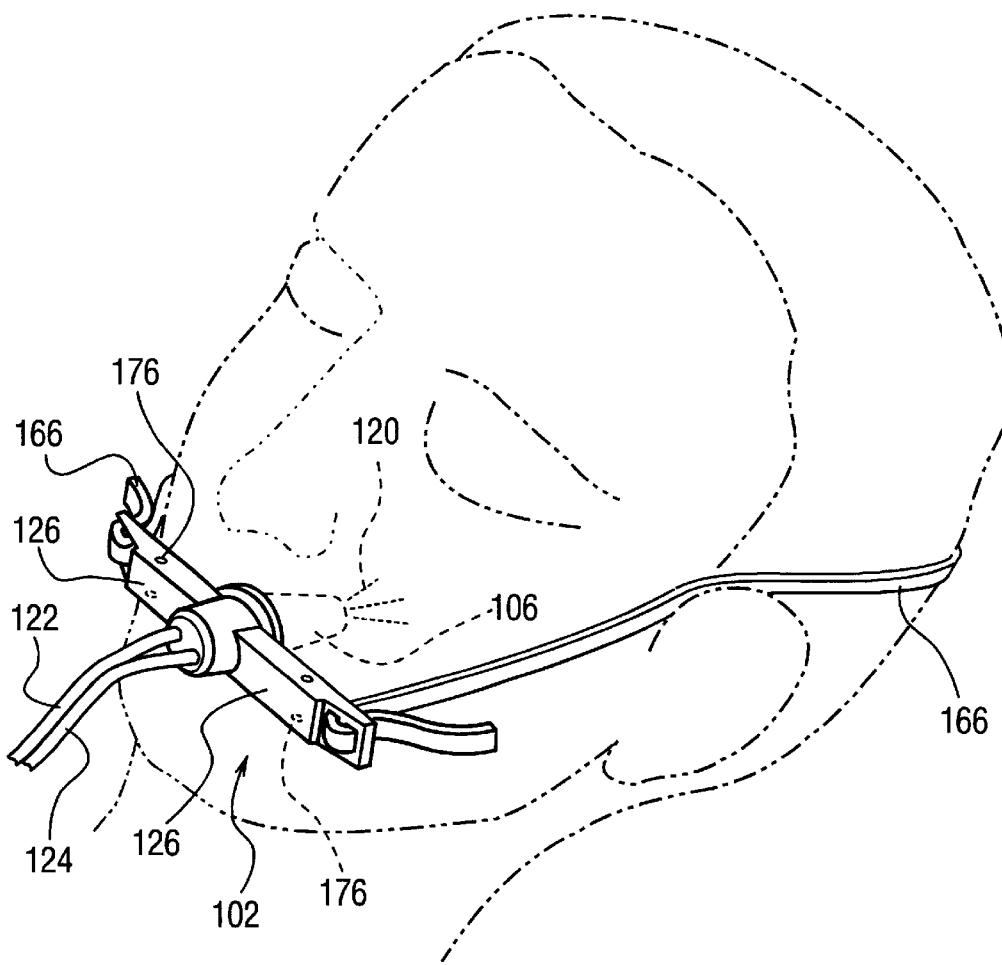
FIG. 18 is a top perspective view of the mouthpiece of FIG. 17.

FIGS. 17 and 18 show a further version of mouth moisturizer system 100. Fins 126 of mouthpiece 102 are straight (non-curved) and fit against the outside of the patient's lips. Each fin 126 has extension 164. In FIG. 17, elastic band segments 166 fit around the patient's head and clamp 168 tightens/secures elastic band (segments) 166. In FIG. 18, elastic band 168 fits around the patient's head with each end thereof looping through two slots in fin extensions 164 for loosening/tightening elastic band 168. As shown in FIG. 17, unit 172 contains air pump 116 and water tank 170. Air pump/compressor 116 provides pressurized air via tube 124 to the downstream side of atomizer 106. Water from water tank 170 is also provided via tube 122 to the downstream side of atomizer 106 by the action created by operation atomizer 106. Orifices 176 in the top and bottom of fins 126 communicate by a passageway (not shown) to the atomizer chamber (not shown). Water mist also exits from orifices onto the lip regions of the patient. Electronic controller 174 is electrically connected to water tank 170 so as to control the opening and closing of water tank 170 to water line 122 (i.e., control the amount and frequency of water released). Electronic controller 174 is electronically connected to air pump 116 so as to control the air pressure and the frequency of movement of pressurized air.

LIST OF NUMBERED ITEMS IN THE DRAWINGS

| Number | Description |
| --- | --- |
| 100 | Mouth moisturizer system |
| 102 | Mouthpiece |
| 104 | Timer |
| 106 | Atomizer |
| 108 | Transformer |
| 110 | Batteries |
| 112 | Hand-held push button controller |
| 114 | Battery/wall transformer selector switch |
| 116 | Air pump (and motor) |
| 118 | Water pump (and motor) |
| 120 | Water mist |
| 122 | Water line |
| 124 | Air line |
| 126 | Mouthpiece fins |
| 128 | Atomizer mist aperture |
| 130 | Mini-pump(s) module |
| 132 | Water supply line |
| 134 | Air supply line |
| 136 | Air filter |
| 138 | Water source |
| 140 | Casing for mini-pumps module 130 |
| 142 | Water bag |
| 144 | Insulated container |
| 146 | Ice pieces |
| 148 | Insulated container top |
| 150 | Probe tube segment |
| 152 | Hooks |
| 154 | Strap |
| 156 | Central portion |
| 158 | Securement rim |
| 160 | Bottom groove |
| 162 | Top groove |
| 164 | Fin extension |
| 166 | Elastic band segment |
| 168 | Clamp to tighten elastic band segments |
| 170 | Water tank |
| 172 | Unit 172 |
| 174 | Controller unit |
| 176 | Orifices |

What is claimed is:

1. A person-operated mouth moisturizer system comprising:
   (a) means for atomizing an aqueous liquid with a gas to form an aqueous liquid mist that is formed and supplied in a controlled, intermittent manner to lips and/or mouth of the person, a portion of said atomizing means being adapted to fit in the mouth of the person;
   (b) means for providing the aqueous liquid and the gas to the atomizer means; and
   (c) triggering device means for the person to control the frequency and amount of and to cause the delivery of aqueous liquid mist supplied, within time strictures of the controlled, intermittent manner of the means (a) for atomizing the aqueous liquid with the gas, to the lips and/or the mouth of the person.

2. The mouth moisturizer system of claim 1, wherein the means (a) for atomizing the aqueous liquid with the gas to form the mist that is supplied in a controlled, intermittent manner includes electronic means to achieve the controlled, intermittent manner of supplying the mist.

3. The mouth moisturizer system of claim 2, wherein the means (b) includes an electrical gas compressor and a tube for transportation of pressurized gas from the gas compressor to the atomizer means.

4. The mouth moisturizer system of claim 3, herein the means (b) further includes a tube for transportation of pressurized aqueous liquid from a source of pressurized aqueous liquid to the atomizer means.

5. The mouth moisturizer system of claim 3, herein the means (b) further includes an electrical pump for pressurizing the aqueous liquid, and a tube for transportation of the pressurized aqueous liquid from the pump to the atomizer means.

6. The mouth moisturizer system of claim 5, wherein the electronic means to achieve the controlled, intermittent manner of supplying the mist is means to control the frequency and duration of operation of the gas compressor and the aqueous liquid pump.

7. The mouth moisturizer system of claim 6, wherein the means to control the frequency and duration of the gas compressor and the aqueous liquid pump is an electrical timer.

8. The mouth moisturizer system of claim 7, wherein the means (c) for the person to control the frequency and amount of the aqueous liquid mist is electronic means.

9. The mouth moisturizer system of claim 8, wherein the electronic means (c) is a hand-held push button momentary switch.

10. The mouth moisturizer system of claim 2, wherein the means (c) for the person to control the frequency and amount of the aqueous liquid mist is electronic means.

11. The mouth moisturizer system of claim 10, wherein the electronic means (c) is a hand-held push button momentary switch.

12. The mouth moisturizer system of claim 2, wherein the aqueous liquid is water.

13. The mouth moisturizer system of claim 12, wherein the aqueous liquid is distilled or sterilized water.

14. The mouth moisturizer system of claim 2, wherein the gas is air.

15. The mouth moisturizer system of claim 9, that also includes a container of aqueous liquid in a unit that is adapted to be mounted on the frame of the patient's bed, and a tube for transporting the aqueous liquid from the container to the aqueous liquid pump.

16. The mouth moisturizer system of claim 2, wherein the atomizer means (a) comprises an elongated atomizer unit that has a fin that is situated perpendicular to its longitudinal axis, mist providing end of said elongated atomizer unit is capable of being positioned in the patient's mouth.

17. The mouth moisturizer system of claim 2, wherein the atomizer means (a) comprises a base that has a curved groove that fits over the lower gum or at least some of the lower teeth of the patient, and an elongated atomizer unit is mounted on said base so that mist providing portion of said elongated aerator unit is capable of being positioned in the patient's mouth.

18. The mouth moisturizer system of claim 2, wherein the atomizer means (a) comprises an atomizer unit having an elongated central portion and two diametrically opposed arm portions, the atomizer unit being capable of providing mist out of at least one aperture in each of the two arms of and/or at least one aperture in the end of the elongated central portion that extends into the patient's mouth.

19. The mouth moisturizer of claim 18, wherein there is an extension on the end of each arm, and elastic band means attached to the unattached end of the arm extensions capable of holding the atomizer unit in the mouth of the patient.

20. A person-operated mouth moisturizer system comprising:
   (a) means for atomizing an aqueous liquid with a gas to form an aqueous liquid mist which is supplied in a controlled manner to lips and/or the mouth of a person, a portion of said atomizing means being adapted to fit in the mouth of the person, said atomizer means comprising an atomizer unit having an elongated central portion and two diametrically opposed arm portions, the atomizer unit being capable of providing mist out of at least one aperture in each of the two arms of and/or at least one aperture in the end of the elongated central portion that extends into the patient's mouth; and
   (b) means for providing the aqueous liquid and the gas to the atomizer means.

21. The mouth moisturizer of claim 20, wherein there is an extension on the end of each arm, and elastic band means attached to the unattached end of the arm extensions capable of holding the atomizer unit in the mouth of the patient.

22. The mouth moisturizer system of claim 20, wherein the aqueous liquid is water.

23. The mouth moisturizer system of claim 22, wherein the aqueous liquid is distilled or sterilized water.

24. The mouth moisturizer system of claim 20, wherein the gas is air.

25. The mouth moisturizer system of claim 20, wherein the means (b) includes a gas compressor and a tube for transportation of pressurized gas from the gas compressor to the atomizer means.

26. The mouth moisturizer system of claim 25, wherein the means (b) further includes a tube for transportation of pressurized aqueous liquid from a source of pressurized aqueous liquid to the atomizer means.

27. The mouth moisturizer system of claim 25, wherein the means (b) further includes a pump for pressurizing the aqueous liquid, and a tube for transportation of the pressurized aqueous liquid from the pump to the atomizer means.

28. The mouth moisturizer system of claim 27, wherein means (b) includes means to control the frequency of and duration of operation of the gas compressor and the aqueous liquid pump.

29. The mouth moisturizer system of claim 28, that also includes a container of aqueous liquid in a unit that is adapted to be mounted on the frame of the patient's bed, and a tube for transporting the aqueous liquid from the container to the aqueous liquid pump.

30. A process of moisturizing lips and/or mouth of a person using a mouth moisturizer system operated by the person, comprising:
   (i) forming a mist in a controlled, intermittent manner by aerating an aqueous liquid with a gas; and
   (ii) supplying the mist in an electronically-controlled, intermittent manner to the lips and/or mouth of the person with the person electronically controlling the frequency and amount, within time strictures of the electronically-controlled, intermittent manner of supplying the mist, of the mist to the lips and/or the mouth of the person.

31. The process of claim 29, wherein the person is recovering from major surgery, the aqueous liquid is water and the gas is air.

32. The process of claim 30, wherein the water is distilled or sterilized water.

33. The process of claim 29, wherein the mist is directed at the lips and/or into mouth of the person.

* * * * *